(12) United States Patent
Wigbers et al.

(10) Patent No.: US 8,637,668 B2
(45) Date of Patent: Jan. 28, 2014

(54) PROCESS FOR PREPARING A CYCLIC TERTIARY METHYLAMINE

(75) Inventors: Christof Wilhelm Wigbers, Mannheim (DE); Johann-Peter Melder, Böhl-Iggelheim (DE); Bernd Stein, Alsbach-Hähnlein (DE); Harald Meiβner, Hassloch (DE)

(73) Assignee: BASF SE, Ludwigshafen (DE)

( * ) Notice: Subject to any disclaimer, the term of this patent is extended or adjusted under 35 U.S.C. 154(b) by 202 days.

(21) Appl. No.: 13/158,667

(22) Filed: Jun. 13, 2011

(65) Prior Publication Data

US 2012/0157679 A1 Jun. 21, 2012

Related U.S. Application Data

(60) Provisional application No. 61/354,753, filed on Jun. 15, 2010.

(51) Int. Cl.
C07D 295/03 (2006.01)

(52) U.S. Cl.
USPC .......................... 544/178; 546/184; 548/579

(58) Field of Classification Search
USPC .......................... 544/178; 546/184; 548/579
See application file for complete search history.

(56) References Cited

U.S. PATENT DOCUMENTS

| | | | |
|---|---|---|---|
| 3,166,558 A | 1/1965 | Mascioli | |
| 3,275,554 A | 9/1966 | Wagenaar | |
| 3,751,475 A | 8/1973 | van der Voort et al. | |
| 3,997,368 A | 12/1976 | Petroff et al. | |
| 4,014,933 A | 3/1977 | Boettger et al. | |
| 4,323,550 A | 4/1982 | Goupil | |
| 4,442,306 A | 4/1984 | Mueller et al. | |
| 4,739,051 A | 4/1988 | Schroeder et al. | |
| 4,832,702 A | 5/1989 | Kummer et al. | |
| 4,845,218 A | 7/1989 | Schroeder | |
| 4,851,578 A | 7/1989 | Fischer et al. | |
| 4,851,580 A | 7/1989 | Mueller et al. | |
| 4,910,304 A | 3/1990 | Fischer et al. | |
| 5,002,922 A | 3/1991 | Irgang et al. | |
| 5,110,928 A | 5/1992 | Schroeder et al. | |
| 5,463,130 A | 10/1995 | Witzel et al. | |
| 5,530,127 A | 6/1996 | Reif et al. | |
| 5,847,131 A | 12/1998 | Simon et al. | |
| 6,187,957 B1 | 2/2001 | Meyer et al. | |
| 6,448,457 B1 | 9/2002 | Hesse et al. | |
| 8,450,530 B2 | 5/2013 | Mueller et al. | |
| 2003/0089591 A1 | 5/2003 | Wolfert et al. | |
| 2005/0000791 A1 | 1/2005 | Wolfert et al. | |
| 2007/0232833 A1 | 10/2007 | Haese et al. | |
| 2008/0064882 A1 | 3/2008 | Huber-Dirr et al. | |
| 2008/0255351 A1 | 10/2008 | Hoffer et al. | |
| 2008/0299390 A1 | 12/2008 | Houssin et al. | |
| 2009/0286977 A1 | 11/2009 | Kubanek et al. | |
| 2010/0274010 A1 | 10/2010 | Kubanek et al. | |
| 2010/0274055 A1 | 10/2010 | Kubanek et al. | |
| 2011/0054167 A1 | 3/2011 | Kubanek et al. | |
| 2011/0137029 A1 | 6/2011 | Kubanek et al. | |
| 2011/0137030 A1 | 6/2011 | Kubanek et al. | |
| 2011/0172430 A1 | 7/2011 | Ernst et al. | |
| 2011/0218270 A1 | 9/2011 | Suter et al. | |
| 2011/0218323 A1 | 9/2011 | Dahmen et al. | |
| 2011/0251433 A1 | 10/2011 | Wigbers et al. | |
| 2011/0251434 A1 | 10/2011 | Muller et al. | |
| 2011/0288337 A1 | 11/2011 | Chedid et al. | |
| 2011/0288338 A1 | 11/2011 | Wigbers et al. | |
| 2011/0294977 A1 | 12/2011 | Schaub et al. | |
| 2012/0035049 A1 | 2/2012 | Kubanek et al. | |
| 2012/0035399 A1 | 2/2012 | Abillard et al. | |
| 2012/0095221 A1 | 4/2012 | Wigbers et al. | |
| 2012/0108816 A1 | 5/2012 | Wigbers et al. | |
| 2012/0157679 A1 | 6/2012 | Wigbers et al. | |

FOREIGN PATENT DOCUMENTS

| | | |
|---|---|---|
| CA | 1046166 | 1/1979 |
| CA | 1055677 | 6/1979 |
| CN | 1634896 A | 7/2005 |
| CN | 1962649 A | 5/2007 |

(Continued)

OTHER PUBLICATIONS

International Search Report—PCT/EP2011/059848—Jun. 14, 2011, dated Jul. 25, 2011.

(Continued)

*Primary Examiner* — Kristin Vajda
(74) *Attorney, Agent, or Firm* — Novak Druce Connolly Bove + Quigg LLP

(57) ABSTRACT

Process for preparing a cyclic tertiary methylamine of the formula I

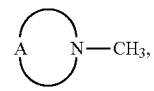

(I)

where
A is a $C_4$-alkylene group, a $C_5$-alkylene group or a —$(CH_2)_2$—B—$(CH_2)_2$— group, where B is oxygen (O) or an N—$R^1$ radical and $R^1$ is $C_1$-$C_5$-alkyl, aryl or $C_5$-$C_7$-cycloalkyl,
wherein
an amino alcohol II from the group consisting of 1,4-aminobutanol, 1,5-aminopentanol, aminodiglycol (ADG) or aminoethylethanolamine of the formula IIa

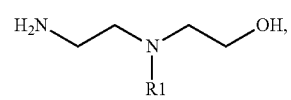

(IIa)

where $R^1$ is as defined above or is hydrogen (H), in which case $R^1$=$CH_3$ in the amine I, is reacted with methanol in a reactor at a temperature in the range from 150 to 270° C. in the liquid phase in the presence of a copper-comprising heterogeneous catalyst.

29 Claims, 1 Drawing Sheet

(56) References Cited

FOREIGN PATENT DOCUMENTS

| | | | |
|---|---|---|---|
| CN | 102101847 A | 6/2011 | |
| CN | 102304101 A | 1/2012 | |
| DE | 917 784 C | 9/1954 | |
| DE | 941 909 C | 4/1956 | |
| DE | 1954546 A1 | 5/1971 | |
| DE | 2125039 A1 | 12/1971 | |
| DE | 1953263 A1 | 2/1972 | |
| DE | 24 45 303 A | 4/1976 | |
| DE | 26 28 087 A | 1/1977 | |
| DE | 2706826 A1 | 9/1977 | |
| DE | 3611230 A1 | 10/1987 | |
| DE | 4021230 | 1/1991 | |
| DE | 40 28 295 A | 3/1992 | |
| DE | 19809418 A1 | 9/1999 | |
| DE | 19859776 A1 | 6/2000 | |
| DE | 10218849 A | 11/2003 | |
| EP | 0 070 512 | 1/1983 | |
| EP | 75940 A1 | 4/1983 | |
| EP | 0 137 478 | 4/1985 | |
| EP | 0 227 904 | 7/1987 | |
| EP | 0 235 651 | 9/1987 | |
| EP | 0 257 443 | 3/1988 | |
| EP | 382049 A1 | 8/1990 | |
| EP | 0 434 062 | 6/1991 | |
| EP | 0 440 829 | 8/1991 | |
| EP | 446783 A2 | 9/1991 | |
| EP | 0 514 692 | 11/1992 | |
| EP | 552 463 | 7/1993 | |
| EP | 599 180 | 6/1994 | |
| EP | 0 673 918 | 9/1995 | |
| EP | 696572 A1 | 2/1996 | |
| EP | 0 816 350 | 6/1996 | |
| EP | 1312599 A1 | 5/2003 | |
| EP | 1312600 A1 | 5/2003 | |
| GB | 1512797 A | 6/1978 | |
| JP | 62145076 A | 6/1987 | |
| WO | WO-92/04119 A1 | 3/1992 | |
| WO | WO-03/051508 A1 | 6/2003 | |
| WO | WO-2004/085356 A1 | 10/2004 | |
| WO | WO 2005/110969 | 11/2005 | |
| WO | WO 2006/005505 | 1/2006 | |
| WO | WO-2006/114417 A2 | 11/2006 | |
| WO | WO 2007/036496 | 4/2007 | |
| WO | WO-2008/006750 A1 | 1/2008 | |
| WO | WO 2008/006754 | 1/2008 | |
| WO | WO 2009/027249 | 3/2009 | |
| WO | WO-2009/080506 A1 | 7/2009 | |
| WO | WO-2009/080507 A1 | 7/2009 | |
| WO | WO-2009/080508 A1 | 7/2009 | |
| WO | WO 2010/031719 | 3/2010 | |
| WO | WO-2010/052181 A2 | 5/2010 | |
| WO | WO-2010/054988 A2 | 5/2010 | |
| WO | WO-2010/069856 A1 | 6/2010 | |
| WO | WO-2010/08926 A2 | 8/2010 | |
| WO | WO-2010/089265 A2 | 8/2010 | |
| WO | WO-2010/089346 A2 | 8/2010 | |
| WO | WO-2010/103062 A1 | 9/2010 | |
| WO | WO-2010/106133 A1 | 9/2010 | |
| WO | WO-2010/115759 A2 | 10/2010 | |
| WO | WO-2010/146009 A1 | 12/2010 | |
| WO | WO-2011/067199 A1 | 6/2011 | |
| WO | WO-2011/067200 A1 | 6/2011 | |
| WO | WO-2011/082967 A1 | 7/2011 | |
| WO | WO-2011/082994 A1 | 7/2011 | |
| WO | WO-2011/107512 A1 | 9/2011 | |
| WO | WO-2011/115759 A1 | 9/2011 | |
| WO | WO-2011/157710 A1 | 12/2011 | |
| WO | WO-2012/049101 A1 | 4/2012 | |

OTHER PUBLICATIONS

U.S. Appl. No. 61/392,960, filed Oct. 14, 2010.
U.S. Appl. No. 61/407,936, filed Oct. 29, 2011.
U.S. Appl. No. 13/906,931, filed May 31, 2013, Chedid et al.
U.S. Appl. No. 13/906,960, filed May 31, 2013, Bou Chedid et al.
U.S. Appl. No. 13/910,602, filed Jun. 5, 2013, Bou Chedid et al.
U.S. Appl. No. 13/284,178, filed Oct. 14, 2011.
U.S. Appl. No. 13/910,554, filed Jun. 5, 2013, Bou Chedid et al.
U.S. Appl. No. 13/284,178, filed Oct. 28, 2013.
Database WPI, Week 198731, Thomson Scientific, London, GA; AN 1987-218358 (XP002664153), & JP 62 145076 A (KOA Corp) Jun. 29, 1987.
International Search Report for PCT/EP2011/067612 dated Nov. 22, 2011.
International Search Report for PCT/EP2011/068700, mailed Feb. 17, 2012.

R = Reactor

K = Distillation column

E = Extraction unit

P = Phase separator

HS = High boilers

KW = Hydrocarbon tert. Amine = cyclic tertiary methylamine I

PROCESS FOR PREPARING A CYCLIC TERTIARY METHYLAMINE

CROSS-REFERENCE TO RELATED APPLICATIONS

This patent application claims the benefit of U.S. provisional patent application Ser. No. 61/354,753 filed Jun. 15, 2010 incorporated in its entirety herein by reference.

FIELD OF THE INVENTION

The present invention relates to a process for preparing a cyclic tertiary methylamine of the formula I where
A is a $C_4$-alkylene group, a $C_5$-alkylene group or a —$(CH_2)_2$—B—$(CH_2)_2$— group, where B is oxygen (O) or an N—$R^1$ radical and $R^1$ is $C_1$-$C_5$-alkyl, aryl or $C_5$-$C_7$-cycloalkyl.

BACKGROUND

Tertiary methylamines are of great importance in the chemical industry for the production of process chemicals, catalysts and intermediates for higher value-added products.

It is known from EP 257 443 A1 (BASF AG) that trialkylamines (e.g. dimethylethylamine) can be prepared by reacting ammonia or primary amines with primary monohydric aliphatic alcohols having from 2 to 24 carbon atoms, preferably in the presence of hydrogen and in the presence of a hydrogenation/dehydrogenation catalyst. The reaction is carried out continuously in the liquid phase at a total pressure of from 50 to 300 bar and a molar excess of from 1 to 15 mol of the alcohol over the ammonia or the primary amine. In addition, the alkylation is carried out in the presence of alkali metal and/or alkaline earth metal oxides and/or hydroxides. The hydrogenation/dehydrogenation catalyst comprises essentially copper. In examples 1 and 3, ammonia is reacted with ethanol or n-butanol in the presence of sodium hydroxide to form triethylamine or tri-n-butylamine. The reaction is carried out at from 230 to 250° C., total pressures of 200 bar and hydrogen partial pressures of >150 bar or 120 bar. Apart from the tertiary amines as target products, only small amounts of secondary amines are formed.

In example 2, the primary amine n-pentylamine is used instead of ammonia and is reacted continuously with n-pentanol in the presence of sodium hydroxide to form tri-n-pentylamine. The molar ratio of n-pentylamine to n-pentanol is 1:4. The reaction temperature is 230-235° C., the total pressure is 60 bar, of which about 10 bar is made up by the hydrogen partial pressure. The molar ratio of tri-n-pentylamine to di-n-pentylamine in the output from the reaction was 1:0.1. Excess n-pentanol was not recirculated to the synthesis step.

According to claim 4, $C_1$-$C_{24}$-alcohols are used in pure form or in the form of their mixtures. Examples using methanol are not present in EP 257 443 A1.

According to EP 227 904 A1 (BASF AG), dimethylamine is reacted with ethanol or n-butanol in a similar way in the liquid phase to give dimethylethylamine or dimethyl-n-butylamine. The reaction is carried out in the presence of alkali metal hydroxide and a catalyst which comprises essentially only copper as active metal or is a pure copper catalyst. It is possible to use monohydric aliphatic alcohols having from 2 to 4 carbon atoms. Methanol is not mentioned in EP 227 904.

A disadvantage of the studies described in EP 257 443 A1 and EP 227 904 A1 is that the alkylation is preferably carried out in the presence of hydrogen. In all examples, the reaction is carried out in the presence of hydrogen. Specific safety measures have to be undertaken for this procedure. In addition, the alkali metal and/or alkaline earth metal oxides and alkali metal or alkaline earth metal hydroxides added to the reaction mixture have to be separated off again from the reaction product mixture after the alkylation reaction. In addition, when methanol is employed and is dehydrogenated to formaldehyde, the Cannizarro reaction can occur and in the presence of the basic alkali metal salts form methanol and alkali metal formate (Beyer/Walther, Lehrbuch der organischen Chemie, 24th edition, 2004, S. Hirzel-Verlag, page 215).

The fact that examples using methanol as alkylating agent are to be found neither in EP 257 443 nor in EP 227 904 may well be attributable to the potentially substantial by-product formation due to the Cannizarro reaction.

U.S. Pat. No. 4,910,304 A (BASF AG) discloses the preparation of N-methylpiperidine and N-methylmorpholine by reaction of pentanediol or diethylene glycol (DEG) with methylamine and 45% strength aqueous KOH solution over an all-active Cu/Al catalyst at 245° C. and 250 bar.

EP 137 478 A (BASF AG) relates to processes for preparing N-methylpiperidine or N-methylmorpholine by catalytic amination of pentanediol by means of methylamine in the gas phase at from 5 to 25 bar over a copper-comprising catalyst which has been obtained by heat treatment of a basic copper- and aluminum-comprising carbonate.

EP 235 651 A1 (BASF AG) teaches a process for preparing N-methylpiperazine from diethanolamine and methylamine over metal-comprising catalysts. The reaction is carried out in the liquid phase (downflow mode) (page 3, last paragraph). According to the example, a Cu/$Al_2O_3$ catalyst is used.

EP 816 350 A1 (BASF AG) describes processes for preparing N-methylpiperidine and N-methylmorpholine by reacting a primary amine with a diol in the liquid or gas phase over a copper catalyst which has been obtained by impregnation of $SiO_2$ spheres with basic copper carbonate.

U.S. Pat. No. 4,739,051 A (BASF AG) teaches the preparation of morpholine and piperidine by reaction of DEG or pentanediol with ammonia under hydrogenating conditions in the gas phase at atmospheric pressure and 200° C. over an all-active Cu/Ni/Al catalyst.

EP 514 692 A2 (BASF AG) discloses processes for preparing amines from alcohols in the presence of catalysts comprising copper and nickel and zirconium oxide and/or aluminum oxide.

EP 440 829 A1 (U.S. Pat. No. 4,910,304) (BASF AG) describes the amination of diols over copper catalysts. The reaction is carried out in the liquid phase (downflow mode) (page 3, last paragraph). Suitable catalysts are the catalysts disclosed in DE 24 45 303 A (BASF AG), which can be obtained by heat treatment of a basic copper- and aluminum-comprising carbonate of the general composition $Cu_mAl_6(CO_3)_{0.5m}O_3(OH)_{m+12}$, where m is any, even nonintegral, number in the range from 2 to 6, for example the copper-comprising precipitated catalyst disclosed in loc. cit., example 1, which is prepared by treating a solution of copper nitrate and aluminum nitrate with sodium bicarbonate and subsequently washing, drying and heating the precipitate.

WO 07/036,496 A1 (BASF AG) describes the reaction of diethylene glycol with ammonia in the presence of Cu—Ni—Co catalysts.

WO 05/110969 A1 (BASF AG) describes a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a copper-comprising catalyst, where the catalytically active composition of the catalyst before reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$) and the reaction is carried out isothermally in the gas phase in a tube reactor.

WO 2010/031719 A1 (BASF SE) relates to a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a copper- and aluminum oxide-comprising catalyst, where the reaction is carried out in the gas phase and the catalytically active composition of the catalyst before reduction with hydrogen comprises aluminum oxide and oxygen-comprising compounds of copper and the shaped catalyst body is specified.

BRIEF SUMMARY

It was an object of the present invention to remedy disadvantages of the prior art and discover an improved economical process for preparing a cyclic tertiary methylamine. In particular, the process should make possible better yields, space-time yields (STY) and selectivities, in particular also without addition of hydrogen.

[Space-time yields are reported in "amount of product/(catalyst volume·time)" (kg/($I_{cat}$·h)) and/or "amount of product/(reactor volume·time)" (kg/($I_{reactor}$·h))].

We have accordingly found a process for preparing a cyclic tertiary methylamine of the formula I where
A is a $C_4$-alkylene group, a $C_5$-alkylene group or a —($CH_2$)—$_2$—B—($CH_2$)$_2$— group, where B is oxygen (O) or an N—$R^1$ radical and $R^1$ is $C_1$-$C_5$-alkyl, aryl or $C_5$-$C_7$-cycloalkyl,
wherein
(i) an amino alcohol II from the group consisting of 1,4-aminobutanol, 1,5-aminopentanol, aminodiglycol (ADG) or aminoethylethanolamine of the formula IIa where $R^1$ is as defined above or is hydrogen (H), in which case $R^1$=$CH_3$ in the amine I, is reacted with methanol in a reactor at a temperature in the range from 150 to 270° C. in the liquid phase in the presence of a copper-comprising heterogeneous catalyst.

Preference is given to separating off unreacted methanol as overhead product from the reaction product mixture from the reaction (reaction step (i)) in a first distillation unit in a subsequent step (ii) and recirculating it to the reaction step (i), with the carbon dioxide content of the recirculated methanol being reduced to such an extent that no solids formation occurs in the methanol feed line to the reactor and the point of entry of the methanol into the reactor.

Further preference is given to water of reaction being removed from the bottom product from the first distillation unit by extraction with aqueous alkali metal hydroxide or alkaline earth metal hydroxide solution or by azeotropic distillation using a hydrocarbon in a second distillation unit in a subsequent step (iii), and (iv) fractionally distilling the resulting output to obtain tertiary amine I.

DETAILED DESCRIPTION OF THE PREFERRED EMBODIMENTS

The process of the invention makes it possible to carry out the substeps of cyclic methylation, namely cyclization and methylation, in one reaction step. Here, the amino alcohols II, IIa are converted with high conversions and yields into the cyclic tertiary methylamine I. Recirculation of incompletely methylated or cyclized intermediates is therefore generally not necessary.

The reaction temperature for the preparation of the tertiary amine I is from 150 to 270° C., preferably from 170 to 250° C., particularly preferably from 180 to 230° C.

According to the stoichiometry of the alkylation by means of methanol, no hydrogen has to be introduced. Thus, in an embodiment of the process, no hydrogen ($H_2$) is introduced into the reactor in reaction step (i).

However, to keep the activity of the hydrogenation catalyst constant over very long times, it can be advantageous to introduce hydrogen continuously or from time to time into the reaction mixture.

The reaction pressure in the reactor is, at the respective reaction temperature, made up of the partial pressures of the starting materials and the reaction products, if applicable of solvent and of hydrogen introduced. The pressure is increased to the desired reaction pressure by injection of hydrogen.

The total pressure (absolute) is preferably from 50 to 150 bar, preferably from 60 to 130 bar, particularly preferably from 70 to 120 bar.

If hydrogen is used, the hydrogen partial pressure, which is made up of that of introduced $H_2$ and $H_2$ generated in-situ, is in particular from 0.01 to 130 bar, preferably from 0.1 to 100 bar, particularly preferably from 1 to 80 bar.

If the alkylation is carried out continuously, the space-time yield is in particular from 0.01 to 5 kg/($I_{cat}$·h), preferably from 0.05 to 3 kg/($I_{cat}$·h), particularly preferably from 0.1 to 1.0 kg/($I_{cat}$·h).

Methanol is preferably used in a significant excess over the amino alcohol (II, IIa) and can serve as reactant and simultaneously as solvent. The molar ratio of amino alcohol to methanol is in particular 1:25, preferably 2:20, particularly preferably 3:15. A high molar ratio can have a positive effect on the selectivity of the tertiary amines I, as long as the excess of methanol does not adversely affect the intramolecular cyclization. In addition, carbamates which may possibly be formed can be dissolved in an excess of methanol.

However, it can also be advantageous to make additional use of a solvent which is inert under the reaction conditions. Aliphatic, cycloaliphatic or aromatic solvents are possible here. Examples are n-hexane, n-octane, cyclohexane, methylcyclohexane, toluene, o-, m- or p-xylene or mixtures of these compounds.

The mixture of amino alcohol, methanol and inert solvent can comprise from 20 to 70% by weight, preferably from 30 to 60% by weight, of an inert solvent.

In a specific embodiment, the reaction is carried out in a plurality of reactors (e.g. 2, 3, 4, 5, etc.) reactors. Preference is given to a combination of two reactors. It is possible here to use identical or different reactors. The reactors can be connected to one another in any way, e.g. in parallel or in series. In a preferred embodiment, two reactors connected in series are used. If a plurality of reactors are used, these can have identical or different temperatures. The temperature in the n-th reactor is preferably at least 10° C. higher, particularly preferably at least 20° C. higher, in particular at least 30° C. higher, than the temperature in the (n−1)-th reactor. The reaction pressure can be identical or different in the individual reactors when a plurality of reactors are used. In a specific embodiment, only some of the reactors comprise catalyst. Thus, for example, it is possible to use a combination of two reactors of which only one comprises catalyst. In this variant, the reaction mixture can firstly be preheated without catalyst in one reactor and then subsequently be transferred for reaction into a reactor with catalyst. To transfer the reaction mixture, it is possible to use, for example, an inert gas such as nitrogen or noble gases or hydrogen, by means of which the mixture is pushed from one reactor into another reactor. In addition, the gas can also serve to set the desired reaction pressure.

Suitable catalysts are in principle hydrogenation catalysts, preferably copper-comprising, heterogeneous catalysts.

Many copper-comprising catalysts which can additionally comprise at least one further element of main group I, II, III, IV or V, of transition group I, II, IV, V, VII or VIII or of the lanthanides (IUPAC: groups 1 to 15 and the lanthanides), in particular Ca, Mg, Al, La, Ti, Zr, Cr, Mo, W, Mn, Ni, Co, Zn and combinations thereof, are suitable in principle. A specific embodiment of advantageous catalysts is Raney catalysts, especially Raney copper and also copper-comprising metal alloys in the form of a Raney catalyst. Preference is given to Raney catalysts whose metal component comprises at least 95% by weight, in particular at least 99% by weight, of copper. Raney copper can be produced in a manner known per se by treating copper-aluminum alloys with alkali metal hydroxides.

A further specific embodiment of catalysts which are particularly advantageous for use in the process are catalysts which comprise copper in oxidic form and, if appropriate, additionally in elemental form.

Suitable catalysts are, for example, catalysts which comprise nickel and copper in addition to other metals as active constituents on a support composed of silica. Such catalysts are described, for example, in DE 26 28 087 A. The active composition of these catalysts comprises, in particular, from 40 to 80% by weight of nickel, from 10 to 50% by weight of copper and from 2 to 10% by weight of manganese. EP 434 062 A describes hydrogenation catalysts which can be obtained by reduction of a precursor composed of oxides of copper, of aluminum and of at least one further metal selected from among magnesium, zinc, titanium, zirconium, tin, nickel and cobalt. The hydrogenation catalysts described in DE 102 18 849 A, which comprise from 0.1 to 10% by weight of chromium, calculated as $Cr_2O_3$, from 0.1 to 10% by weight of calcium, calculated as $CaO_x$ and from 5 to 20% by weight of copper, calculated as CuO, deposited on a silicon dioxide support material, in each case based on the total weight of the calcined catalyst, are also suitable. DE 40 21 230 A discloses copper-zirconium oxide catalysts in which the ratio of copper atoms to zirconium atoms, expressed as weight ratio, is from 1:9 to 9:1. DE 4 028 295 A describes suitable copper-manganese hydrogenation catalysts. EP 552 463 A describes catalysts which in oxidic form have essentially the composition $Cu_aAl_bZr_cMn_dO_x$, where the following relationships apply: a>0; b>0; c≥0; d>0; a>b/2; b>a/4; a>c; a>d; and x denotes the number of oxygen ions required to ensure electrical neutrality per formula unit. EP 552 463 A also describes catalysts having a low proportion of aluminum oxide. The catalyst of this embodiment corresponds essentially to the composition $Cu_aAl_bZr_cMn_dO_x$, where the following relationships apply: a>0; a/40≤b≤a/4; c≥0; d>0; a>c; 0.5d≤a≤0.95d and x denotes the number of oxygen ions required to ensure electrical neutrality per formula unit. WO 2006/005505 A describes shaped catalyst bodies which are particularly suitable for use in the process of the invention. In a preferred embodiment, the oxidic catalyst material comprises (a) copper oxide in a proportion such that 50≤x≤80% by weight, preferably 55≤x≤75% by weight,
(b) aluminum oxide in a proportion such that 15≤y≤35% by weight, preferably 20≤y≤30% by weight, and
(c) at least one of the oxides of lanthanum, tungsten, molybdenum, titanium or zirconium, preferably of lanthanum and/or tungsten, in a proportion such that 2≤z≤20% by weight, preferably 3≤z≤15% by weight, in each case based on the total weight of the oxidic material after calcination, where: 80≤x+y+z≤100, in particular 95≤x+y+z≤100.

Preferred catalysts comprise the following metals in oxidic form, reduced form (elemental form) or a combination thereof. Metals which are stable in more than one oxidation state can be used entirely in one of the oxidation states or in various oxidation states:

Cu
Cu, Ti
Cu, Zr
Cu, Mn
Cu, Al
Cu, Ni, Mn
Cu, Al, at least one further metal selected from among La, W, Mo, Mn, Zn, Ti, Zr, Sn, Ni, Co
Cu, Zn, Zr
Cu, Cr, Ca
Cu, Cr, C
Cu, Al, Mn, if appropriate Zr.

As inert support material for the catalysts used according to the invention, it is possible to employ virtually all support materials of the prior art which can advantageously be used in the production of supported catalysts, for example $SiO_2$ (quartz), porcelain, magnesium oxide, tin dioxide, silicon carbide, $TiO_2$ (rutile, anatase), $Al_2O_3$ (alumina), aluminum silicate, steatite (magnesium silicate), zirconium silicate, cerium silicate or mixtures of these support materials. Preferred support materials are aluminum oxide and silicon dioxide.

In a preferred embodiment of the process of the invention, copper catalysts as described in DE 2 445 303 A1 (BASF AG) are used. They can be considered to be amorphous products of the thermal decomposition and reduction of basic copper-aluminum carbonates and are obtained by precipitating dilute or moderately concentrated, advantageously less than 3 molar, solutions of copper and aluminum salts by means of alkali metal carbonate at pH 8-10 and decomposing the resulting precipitates before or after appropriate shaping at a temperature of 350-600° C. After customary reduction, preferably in the presence of the alcohol used in the later reaction, highly active catalysts which are best suitable for the present process are obtained.

In the suspension mode which is likewise possible according to the process of the invention, the reduced copper catalyst is suspended in the reaction components alcohol and amines. Suitable catalysts are, for example, Raney copper or the above-described copper catalysts in powdered form. However, preference is given to a copper material obtained by heating copper formate to 200-250° C. in the presence of an alcohol and dialkylamine. The formation of such a catalyst is described, for example, in EP 70 512 A.

The catalysts can be used as shaped bodies, e.g. in the form of spheres, rings, cylinders, cubes, cuboids or other geometric bodies. Unsupported catalysts can be shaped by customary methods, e.g. by extrusion, tableting, etc. The shape of supported catalysts is determined by the shape of the support. As an alternative, the support can be subjected to a shaping process before or after application of the catalytically active component(s). The catalyst can, for example, be used in the form of pressed cylinders, tablets, pastilles, wagon wheels, rings, stars or extrudates such as solid extrudates, polylobal extrudates, hollow extrudates and honeycomb bodies or other geometric bodies.

In the process of the invention, the catalysts are particularly preferably used in the form of catalysts which consist entirely of catalytically active composition and, if appropriate, a shaping aid (e.g. graphite or stearic acid) if the catalyst is used as shaped bodies, i.e. comprise no further catalytically active constituents.

In this context, oxidic support material, particularly preferably aluminum oxide ($Al_2O_3$), is counted as part of the catalytically active composition.

The catalysts are preferably used by milling the catalytically active composition, mixing it with shaping aids, shaping and heating to give shaped catalyst bodies, e.g. tablets, spheres, rings, extrudates (e.g. rods), and arranging the shaped bodies in the reactor.

The concentrations (in % by weight) indicated for the components of the catalyst are in each case, unless indicated otherwise, based on the catalytically active composition of the finished catalyst after its last heat treatment and before reduction with hydrogen.

The catalytically active composition of the catalyst after its last heat treatment and before reduction with hydrogen is defined as the sum of the masses of the catalytically active constituents and the abovementioned catalyst support material and preferably comprises essentially the following constituents:
aluminum oxide ($Al_2O_3$) and oxygen-comprising compounds of copper and preferably oxygen-comprising compounds of sodium.

The sum of the abovementioned constituents of the catalytically active composition, calculated as $Al_2O_3$, CuO and $Na_2O$, is usually from 70 to 100% by weight, preferably from 80 to 100% by weight, particularly preferably from 90 to 100% by weight, more preferably from 98 to 100% by weight, more preferably 99% by weight, very particularly preferably 100% by weight.

The catalytically active composition of the catalysts used in the process of the invention can further comprise one or more elements (oxidation state 0) or inorganic or organic compounds thereof selected from groups I A to VI A and I B to VII B and VIII of the Periodic Table.

Examples of such elements and compounds thereof are: transition metals such as Ni and NiO, Co and CoO, Re and rhenium oxides, Mn and $MnO_2$, Mo and molybdenum oxides, W and tungsten oxides, Ta and tantalum oxides, Nb and niobium oxides or niobium oxalate, V and vanadium oxides and vanadyl pyrophosphate; lanthanides such as Ce and $CeO_2$ or Pr and $Pr_2O_3$; alkali metal oxides such as $K_2O$; alkali metal carbonates such as $Na_2CO_3$; alkaline earth metal oxides such as CaO, SrO; alkaline earth metal carbonates such as $MgCO_3$, $CaCO_3$ and $BaCO_3$; boron oxide ($B_2O_3$).

The catalytically active composition of the catalysts used in the process of the invention comprises, after its last heat treatment and before reduction with hydrogen, in particular from 25 to 80% by weight, preferably from 30 to 70% by weight, particularly preferably from 35 to 60% by weight, of aluminum oxide ($Al_2O_3$) and
from 20 to 75% by weight, preferably from 30 to 70% by weight, particularly preferably from 40 to 65% by weight, very particularly preferably from 45 to 60% by weight, of oxygen-comprising compounds of copper, calculated as CuO,
from 0 to 2% by weight, preferably from 0.05% to 1% by weight, particularly preferably from 0.1 to 0.5% by weight, of oxygen-comprising compounds of sodium, calculated as $Na_2O$,
less than 5% by weight, e.g. from 0.1 to 4% by weight, preferably less than 1% by weight, e.g. from 0 to 0.8% by weight, of oxygen-comprising compounds of nickel, calculated as NiO.

The catalytically active composition of the catalyst before reduction with hydrogen particularly preferably comprises less than 1% by weight, e.g. from 0 to 0.5% by weight, of oxygen-comprising compounds of cobalt, calculated as CoO.

The catalytically active composition of the catalyst used in the process of the invention very particularly preferably does not comprise any nickel, cobalt and/or ruthenium, in each case neither in metallic form (oxidation state 0) nor in an ionic, in particular oxidized, form.

Oxygen-comprising compounds of copper are, in particular, copper(I) oxide and copper(II) oxide, preferably copper (II) oxide.

The catalytically active composition of the catalyst used in the process of the invention very particularly preferably does not comprise any zirconium dioxide ($ZrO_2$), titanium dioxide ($TiO_2$) and/or silicon dioxide ($SiO_2$).

In a particularly preferred embodiment, the catalytically active composition of the catalysts used in the process of the invention does not comprise any further catalytically active component, neither in elemental form nor in ionic form.

In the particularly preferred embodiment, the catalytically active composition is not doped with further metals or metal compounds.

However, customary accompanying trace elements originating from the metal winning of Cu or if appropriate Ni are preferably excluded therefrom.

Various methods are possible for producing the catalysts used in the process of the invention. They can be obtained, for example, by peptizing pulverulent mixtures of hydroxides, carbonates, oxides and/or other salts of the components aluminum, copper, if appropriate sodium by means of water and subsequently extruding and heat treating the resulting composition.

The catalysts which are preferably used in the process of the invention can also be produced by impregnating aluminum oxide ($Al_2O_3$), which is present, for example, in the form of powder or shaped tablets.

Aluminum oxide can be used in various modifications, with preference being given to α- (alpha), γ- (gamma) or θ-$Al_2O_3$ (theta-$Al_2O_3$). Particular preference is given to using γ-$Al_2O_3$.

The production of shaped bodies of aluminum oxide can be carried out by the usual methods.

The impregnation of the aluminum oxide is likewise carried out by the usual methods, as described, for example, in EP 599 180 A, EP 673 918 A or A. B. Stiles, Catalyst Manufacture—Laboratory and Commercial Preparations, Marcel Dekker, New York (1983), by applying an in each case appropriate metal salt solution in one or more impregnation steps, with the metal salts used being, for example, the corresponding nitrates, acetates or chlorides. After the impregnation, the composition is dried and if appropriate calcined.

The impregnation can be carried out by the "incipient wetness" method, in which the inorganic oxide (i.e. aluminum oxide) is moistened with the impregnation solution to not more than saturation according to its water uptake capacity. However, the impregnation can also be carried out in a supernatant solution.

In multistage impregnation methods, it is advantageous to dry and if appropriate calcine the inorganic oxide between individual impregnation steps. Multistage impregnation can be used particularly advantageously when the inorganic oxide is to be loaded with a relatively large amount of metal.

To apply a plurality of metal components to the inorganic oxide, the impregnation can be carried out with, if appropriate, all metal salts simultaneously or in any order of the individual metal salts.

Preference is given to employing precipitation methods for producing the catalysts which are preferably used in the process of the invention. Thus, they can be obtained, for example, by coprecipitation of the components from an aqueous salt solution by means of mineral bases in the presence of a slurry of a sparingly soluble, oxygen-comprising aluminum compound and subsequent washing, drying and calcination of the precipitate obtained. As sparingly soluble, oxygen-comprising aluminum compound, it is possible to use, for example, aluminum oxide. The slurry of the sparingly soluble aluminum compound can be produced by suspending fine powders of this compound in water with vigorous stirring. These slurries are advantageously obtained by precipitation of the sparingly soluble aluminum compound from aqueous aluminum salt solutions by means of mineral bases.

The catalysts which are preferably used in the process of the invention are preferably produced by coprecipitation of all their components. For this purpose, it is advantageous to admix an aqueous salt solution comprising the catalyst components with an aqueous mineral base, in particular an alkali metal base, for example sodium carbonate, sodium hydroxide, potassium carbonate or potassium hydroxide, hot and with stirring until precipitation is complete. The type of salts used is generally not critical: since in this procedure the important thing is primarily the solubility of the salts in water, a criterion is that they have the good solubility in water required to produce these relatively highly concentrated salt solutions. It goes without saying that when selecting the salts of the individual components, only salts having anions which do not lead to interference, whether by causing undesirable precipitations or inhibiting or preventing precipitation by complex formation, will naturally be selected.

The precipitates obtained in these precipitation reactions are generally chemically uniform and comprise, inter alia, mixtures of the oxides, oxide hydrates, hydroxides, carbonates and insoluble and basic salts of the metal/metals used. It can be advantageous in terms of the filterability of the precipitates to age the precipitates, i.e. to leave them standing for some time after the precipitation, if appropriate at elevated temperature or while passing air through the mixture.

The precipitates obtained by these precipitation processes are processed further in a customary manner to give the catalysts used according to the invention. After washing, they are preferably dried at from 80 to 200° C., more preferably from 100 to 150° C., and then calcined. Calcination is preferably carried out at temperatures in the range from 300 to 800° C., more preferably from 400 to 600° C., in particular from 450 to 550° C.

After calcination, the catalyst is advantageously conditioned, either by milling to set a particular particle size and/or by mixing with shaping aids such as graphite or stearic acid after milling, pressing by means of a press to give shaped bodies, namely pellets, and heat treated. The heat treatment temperatures preferably correspond to the temperatures in the calcination.

The catalysts produced in this way comprise the catalytically active metals in the form of a mixture of their oxygen-comprising compounds, i.e. in particular as oxides and mixed oxides.

The catalysts produced in this way can be stored as such. They are usually prereduced before use as catalysts. However, they can also be used without prereduction, in which case they are then reduced by the hydrogen present in the reactor under the conditions of the hydrogenating amination.

To carry out prereduction, the catalysts are firstly exposed to a nitrogen-hydrogen atmosphere at preferably from 150 to 200° C. over a period of, for example, from 12 to 20 hours and subsequently treated in a hydrogen atmosphere at preferably from 200 to 400° C. for a period of up to about 24 hours. During this prereduction, part of the oxygen-comprising metal compound(s) present in the catalysts is/are reduced to the corresponding metal(s), so that these are present together with the various oxygen compounds in the active form of the catalyst.

The reaction according to the process of the invention is preferably carried out in a tube reactor.

In a single line plant, the tube reactor in which the preferably isothermal reaction is carried out comprises a series arrangement of a plurality of (e.g. two or three) individual tube reactors.

The preferably isothermal reaction according to the process of the invention is preferably carried out with a temperature deviation of not more than +/−8° C., in particular not more than +/−5° C., particularly preferably not more than +/−4° C., very particularly preferably not more than +/−3° C., e.g. not more than from +/−0 to +/−2° C. or not more than from +/−0 to +/−1° C.

These temperature deviations relate to the respective temperatures in the respective catalyst bed, at the point where the starting materials enter the catalyst bed and the point where the reaction mixture leaves the catalyst bed. It is possible to connect a plurality of catalyst beds in parallel or in series.

If a plurality of catalyst beds are connected in series, the abovementioned temperature deviations in the isothermal mode of operation which is preferred according to the invention relate to the respective temperature in the catalyst bed, at the point at which the starting materials enter the first catalyst bed and the point at which the reaction mixture leaves the last catalyst bed.

In a preferred embodiment, the temperature of the tube reactor is controlled from the outside by means of a stream of heat transfer medium, with the heat transfer medium being able to be, for example, an oil, a salt melt or another heat-transferring liquid.

The process of the invention is preferably carried out continuously, with the catalyst preferably being arranged as a fixed bed in the reactor. The reaction mixture can be passed through the fixed catalyst bed either from the top or from below.

The water of reaction formed during the reaction generally does not have an adverse effect on the conversion, the reaction rate, the selectivity and the operating life of the catalyst and is therefore advantageously removed from the reaction product only in the work-up of the latter, e.g. by distillation.

The liquid reaction product mixture obtained after cooling and depressurization is, if appropriate, separated from suspended catalysts. The catalyst-free reaction product mixture comprises the target product, viz. the tertiary methylamine I, together with excess alcohol and water formed. Depending on the number of methylation steps, two to three mol of water are formed, depending on and based on the amino alcohol (II, IIa) used. In addition, unreacted amino alcohol, intermediates which have not been completely alkylated and possibly small amounts of amino alcohol by-products may also be present.

Figure 1A:
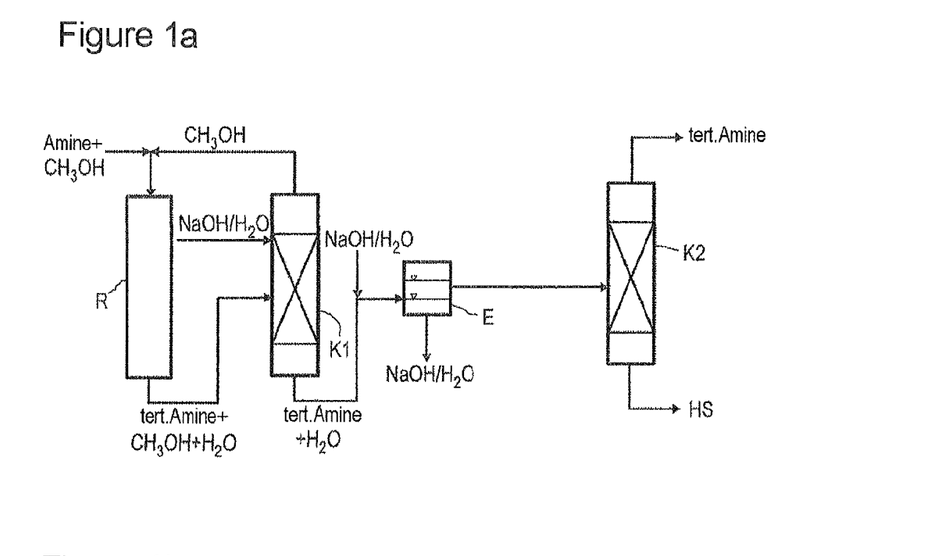
FIGS. 1A-1B depict preferred embodiments of the processes for preparing a cyclic tertiary methylamine.
Figure 1B:
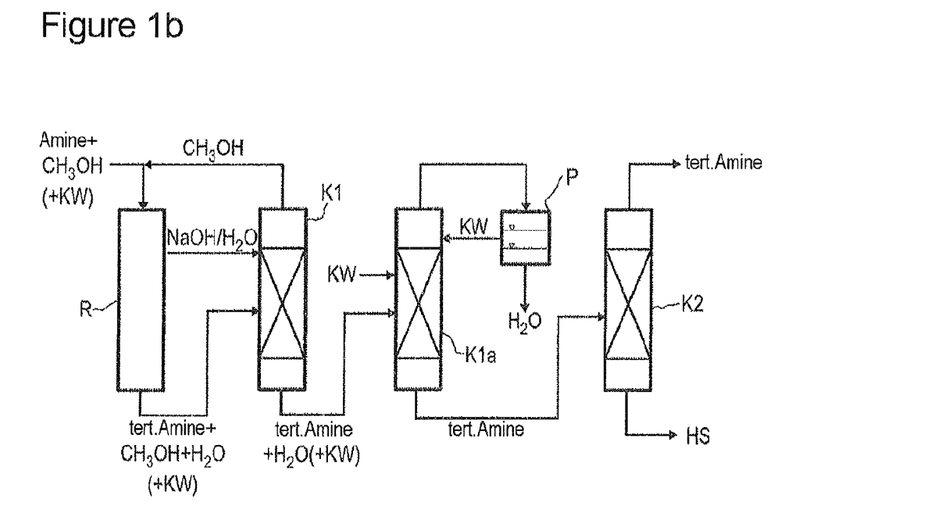

The work-up is carried out, in particular, by distillation (cf. FIGS. 1 a and 1 b for preferred embodiments).

According to the invention, it has also been recognised that:
if excess methanol was distilled off overhead from the reaction product mixture, e.g. in a first distillation column K 1, and mixed with fresh amino alcohol (II, IIa), encrustations and blockages due to solids occurred in the feed pipe to the reactor and at the entry point into the reactor unless the two streams or the total stream were preheated at a temperature of <50° C., in particular <40° C. Since carbon dioxide could be detected in the reaction product mixture, the solids could be carbamates.

The encrustations and blockages were able to be prevented by introducing an aqueous solution of alkali metal or alkaline earth metal hydroxides, e.g. at the top of the distillation column K1.

Accordingly, an aqueous solution of an alkali metal hydroxide or alkaline earth metal hydroxide is introduced into the first distillation unit in step (ii) in a particularly preferred process variant. The amount of alkali metal hydroxide or alkaline earth metal hydroxide is preferably from 0.0001 to 0.1 mol per mol of methanol.

The amount of water is not critical since this can be separated off together with the water of reaction. Preference is given to aqueous solutions comprising from 20 to 50% by weight of alkali metal or alkaline earth metal hydroxides, preferably sodium hydroxide and potassium hydroxide.

When, by means of this measure, methanol was recirculated, e.g. via the top of the column K 1, mixed with fresh amino alcohol (II, IIa), preheated to temperatures in the range from 130 to 270° C. and fed into the reactor, no solids formation occurred.

According to the invention, in a step (ii), the carbon dioxide content of the recirculated methanol is preferably reduced in one embodiment preferably by stripping the recycle methanol in the liquid phase with an inert gas such as $N_2$ or Ar at a temperature in the range from 0 to 230° C., in particular from 5 to 170° C., more particularly from 10 to 85° C. This stripping is preferably carried out for a period of from 0.1 minute to 5 hours, particularly preferably from 1 minute to 1 hour. To ensure that the methanol remains in the liquid phase, a superatmospheric pressure, e.g. from 1 to 100 bar, has to be employed at elevated temperatures.

In another embodiment, in step (ii), the carbon dioxide content of the recirculated methanol is preferably reduced by heating the recycle methanol in the liquid phase to a temperature in the range from 20 to 120° C., particularly preferably from 30 to 65° C. This heating is preferably carried out for a period of from 1 minute to 24 hours, particularly preferably from 1 minute to 12 hours. To ensure that the methanol remains in the liquid phase, a superatmospheric pressure, e.g. from 1 to 10 bar, has to be employed at elevated temperatures.

The carbon dioxide content of the recirculated methanol is preferably reduced to such an extent that no solids formation occurs in the methanol feed line to the reactor, in the reactor and in particular at the point of entry of the methanol into the reactor. The methanol feed line to the reactor includes the line to any preheater present upstream of the reactor.

In particular, the carbon dioxide content of the recirculated methanol is reduced in step (ii) to a value in the range from 0 to 15 mol %, in particular from 0.001 to 5 mol % (in each case based on methanol).

In a continuous mode of operation, amino alcohol (II, IIa) and recycle methanol from step (ii) are preferably introduced in two separate streams rather than a combined stream into the reactor of reaction step (i).

In particular, the recycle methanol from step (ii) and the amino alcohol are preheated either individually or as a mixture to a temperature in the range from 20 to 240° C., particularly preferably from 40 to 150° C., more particularly from 50 to 100° C., before introduction into the reactor of reaction step (i).

Particular preference is given to a combination of preheating, in particular the recycle methanol, with lowering of the carbon dioxide content.

The bottom product from the methanol distillation, e.g. from the column K 1, can be extracted with from 20 to 50% strength by weight aqueous alkali metal or alkaline earth metal hydroxide solution to separate off the water of reaction. The aqueous hydroxide solution is separated off by phase separation and discharged, and the organic phase is preferably distilled in a further distillation unit, e.g. column K 2, in such a way that the tertiary amine I is obtained as overhead product and high boilers (HS) are obtained as bottom product (cf. FIG. 1 a).

This dewatering method (cf. FIG. 1 a) has the advantage that the mixture of alkali metal and alkaline earth metal carbonate and alkali metal and/or alkaline earth metal hydroxide obtained as distillation bottoms, e.g. at the bottom of column K 1, can be separated off or discharged together with the aqueous hydroxide solution introduced for dewatering.

In a further preferred embodiment of the methylation by means of methanol, the distillation bottoms after methanol has been separated off, e.g. the bottom stream from the column K 1, which may already comprise a hydrocarbon (in particular $C_4$-$C_{10}$-hydrocarbon such as heptanes, octanes, cyclohexanes, cycloheptanes) as solvent, is fed to a further distillation unit, e.g. column K 1a. If necessary, a further amount of the hydrocarbon is fed into the further distillation column, e.g. the column K 1a. A two-phase hydrocarbon/water azeotrope is distilled off overhead by azeotropic distillation. In the phase separator P, the water phase is discharged and the hydrocarbon phase is returned to the top of the column. The bottom stream from column K 2 is, e.g. as shown in FIG. 1 a, fed to a further distillation unit, e.g. the column K 2, to obtain pure tertiary amine I (cf. FIG. 1 b).

The process of the invention can be used to prepare tertiary amines of the formula I (I)

where

A is a $C_4$-alkylene group, a $C_5$-alkylene group or a —$(CH_2)$—$_2$—B—$(CH_2)_2$— group, where B is oxygen (O) or an N—$R^1$ radical and $R^1$ is $C_1$-$C_5$-alkyl, aryl or $C_5$-$C_7$-cycloalkyl, by reacting an amino alcohol II from the group consisting of 1,4-aminobutanol, 1,5-aminopentanol, aminodiglycol (ADG) or aminoethylethanolamine of the formula IIa (IIa)

where $R^1$ is as defined above or is hydrogen (H), in which case $R^1$=$CH_3$ in I, with methanol.

Preference is given to the preparation of N-methylpyrrolidine by reaction of 1,4-aminobutanol.

Preference is also given to the preparation of N-methylpiperidine by reaction of 1,5-aminopentanol.

Preference is also given to the preparation of N-methylmorpholine by reaction of aminodiglycol (ADG).

Further preference is given to the preparation of N,N'-dimethylpiperazine by reaction of aminoethylethanolamine of the formula IIa (IIa)

where $R^1$ is hydrogen (H) or methyl.

The substituent $R^1$ in the compounds I and IIa has the following meanings:

$R^1$:

$C_{1-5}$-alkyl, preferably $C_{1-3}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, $C_{5-7}$-cycloalkyl, preferably $C_{5-6}$-cycloalkyl, such as cyclopentyl, cyclohexyl, cycloheptyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, in IIa also hydrogen (H), in which case $R^1$=$CH_3$ in the reaction product I.

The synthesis of the amines I can be referred to as a cyclizing methylation. The cyclizing methylation of 1,4-aminobutanol can occur via the intermediates

The cyclizing methylation of 1,5-aminopentanol can occur via the intermediates

The cyclizing methylation of aminodiglycol ($H_2N(CH_2)_2$—O—$(CH_2)_2OH$, ADG) can occur via the intermediates The cyclizing methylation of aminoethylethanolamine of the formula IIa with $R^1$=H can occur via the intermediates The cyclizing methylation of aminoethylethanolamine of the formula IIa with $R^1$=$CH_3$ can occur via the intermediates All pressures reported are absolute pressures.

EXAMPLES

A copper catalyst having the composition 55% by weight of CuO and 45% by weight of gamma-$Al_2O_3$ (after its last heat treatment and before reduction with hydrogen) (catalyst A) was used for the following examples.

The catalyst was produced by impregnating gamma-$Al_2O_3$ powder with an aqueous copper nitrate solution. Tableting was carried out by the customary method. Before commencement of the reaction, the catalyst was reduced in a stream of hydrogen at about 200° C. (see below).

Example 1

Preparation of N,N'-dimethylpiperazine from aminoethylethanolamine and methanol The reaction was carried out in a magnetically coupled 300 ml stirring autoclave provided with electric heating and internal temperature cascade regulation. 15.6 g of aminoethylethanolamine (IIa1) (0.15 mol), 102.1 g of methanol (3.2 mol) and 15 g of a reduced and passivated catalyst A comprising copper on aluminum oxide (3×3 mm pellets) were introduced into the autoclave which had been made inert by means of nitrogen. The catalyst comprised, before reduction, 55% by weight of copper oxide (CuO) and 45% by weight of aluminum oxide. The reduction was carried out before the reaction at 180 to 200° C., and the passivation was carried out at <50° C. by means of air. The reaction mixture was pressurized at room temperature with hydrogen up to a pressure of 10 bar. The autoclave was then heated to 200° C., further hydrogen was injected to a total pressure of 80 bar and the reaction mixture was stirred at 200° C. and 80 bar (800 rpm) for 12 hours.

Gas-chromatographic analysis (GC column 30 m RTX 5 Amin) indicated that the reaction product mixture (without excess methanol) at complete aminoethylethanol-amine conversion comprised 88.5% by area of N,N'-dimethylpiperazine.

It is known from example 2 in EP 257 443 B1 that the primary amine n-pentylamine can be reacted with the primary alcohol n-pentanol in the presence of copper catalysts to form the tertiary amine tri-n-pentylamine. It would therefore have been expected that aminoethylethanolamine IIa1 would be converted entirely or at least partly into N,N'-dimethylaminoethylethanolamine III with $R^1$=H and/or its methylation product III with $R^1$=CH$_3$.

Both compounds III cannot undergo cyclization to N,N'-dimethylpiperazine. III was not found by gas chromatography. This result and the high yields of N,N'-dimethylpiperazine are therefore surprising to a person skilled in the art.

The same reasoning for a surprising result applies to other starting compounds II, e.g. 1,4-aminobutanol, 1,5-aminopentanol and aminodiglycol (ADG).

Example 2

Preparation of N-methylmorpholine from Aminodiglycol and Methanol

Example 2 was carried out in the apparatus described in example 1. 15.7 g of aminodiglycol (0.15 mol), 96 g of methanol (3 mol) and 10 g of the reduced and passivated catalyst (A) described in example 1 were introduced into the autoclave which had been made inert by means of nitrogen. The reaction mixture was pressurized at room temperature with 10 bar of hydrogen. The autoclave was then heated to 180° C. and further hydrogen was injected to a pressure of 80 bar. The reaction mixture was stirred at 180° C. and 80 bar (700 rpm) for 6 hours. The autoclave was then cooled and depressurized. Gas-chromatographic analysis (GC column and analytical conditions as in example 1) indicated that the reaction product mixture at complete conversion of the aminodiglycol comprised 85.5% by area of N-methylmorpholine.

Example 3

Preparation of N-methylpiperidine from 5-aminopentanol and Methanol

Example 3 was carried out in the apparatus described in example 1. 31 g of 5-aminopentanol (0.3 mol), 102 g of methanol (3.2 mol) and 3 g of the reduced and passivated catalyst (A) described in example 1 were introduced into the autoclave which had been made inert by means of nitrogen. The reaction mixture was pressurized at room temperature with 5 bar of hydrogen. The autoclave was then heated to 200° C. and further hydrogen was injected to a pressure of 80 bar. The reaction mixture was stirred at 200° C. and 80 bar (800 rpm) for 12 hours. The autoclave was then cooled and depressurized. Gas-chromatographic analysis (GC column and ana- lytical conditions as in example 1) indicated that the reaction product mixture at complete conversion of the 5-aminopentanol comprised 88% by area of N-methylpiperidine.

The invention claimed is:

1. A process for preparing a cyclic tertiary methylamine of the formula I where
A is a $C_4$-alkylene group, a $C_5$-alkylene group or a —$(CH_2)_2$—B—$(CH_2)_2$— group, where B is oxygen (O) or an N—$R^1$ radical and $R^1$ is $C_1$-$C_5$-alkyl, aryl or $C_5$-$C_7$-cycloalkyl,
wherein
(i) an amino alcohol II from the group consisting of 1,4-aminobutanol, 1,5-aminopentanol, aminodiglycol (ADG) or aminoethylethanolamine of the formula IIa where $R^1$ is as defined above or is hydrogen (H), in which case $R^1$=$CH_3$ in the amine I, is reacted with methanol in a reactor at a temperature in the range from 150 to 270° C. in the liquid phase in the presence of a copper-comprising heterogeneous catalyst.

2. The process according to claim 1, wherein
(ii) unreacted methanol is separated off as overhead product from the reaction product mixture from the reaction (reaction step (i)) in a first distillation unit and recirculated to the reaction step (i), with the carbon dioxide content of the recirculated methanol being reduced to such an extent that no solids formation occurs in the methanol feed line to the reactor and the point of entry of the methanol into the reactor.

3. The process according to claim 2, wherein
(iii) water of reaction is removed from the bottom product from the first distillation unit by extraction with aqueous alkali metal hydroxide or alkaline earth metal hydroxide solution or by azeotropic distillation using a hydrocarbon in a second distillation unit and (iv) the resulting output is fractionally distilled to obtain tertiary amine I.

4. The process according to claim 2, wherein, in step (ii), the carbon dioxide content of the recirculated methanol is reduced by heating the recycle methanol in the liquid phase to a temperature in the range from 20 to 120° C.

5. The process according to claim 2, wherein, in step (ii), the carbon dioxide content of the recirculated methanol is reduced by stripping the recycle methanol in the liquid phase with an inert gas at a temperature in the range from 0 to 230° C.

6. The process according to claim 2, wherein, in step (ii), the carbon dioxide content of the recirculated methanol is reduced to a value in the range from 0 to 15 mol %.

7. The process according to claim 2, wherein an aqueous solution of an alkali metal hydroxide or alkaline earth metal hydroxide is introduced into the first distillation unit in step (ii).

8. The process according to claim 7, wherein the amount of alkali metal or alkaline earth metal hydroxide is from 0.0001 to 0.1 mol per mol of methanol.

9. The process according to claim 1, wherein the reaction of the amino alcohol (II, IIa) with methanol (step (i)) is carried out continuously.

10. The process according to claim 9, wherein amino alcohol and recycle methanol from step (ii) are introduced in two separate streams or together into the reactor of reaction step (i).

11. The process according to claim 10, wherein the recycle methanol from step (ii) and the amino alcohol are preheated individually or as a mixture to a temperature in the range from 20 to 240° C. before introduction into the reactor of reaction step (i).

12. The process according to claim 1 for the preparation of N-methyl-pyrrolidine by reaction of 1,4-aminobutanol.

13. The process according to claim 1 for the preparation of N-methylpiperidine by reaction of 1,5-aminopentanol.

14. The process according to claim 1 for the preparation of N-methylmorpholine by reaction of aminodiglycol (ADG).

15. The process according to claim 1 for the preparation of N,N'-dimethylpiperazine by reaction of aminoethylethanolamine of the formula IIa where $R^1$ is hydrogen (H) or methyl.

16. The process according to claim 1, wherein the reaction is carried out in the presence of a copper- and aluminum oxide-comprising catalyst.

17. The process according to claim 1, wherein the catalytically active composition of the catalyst before reduction with hydrogen comprises
from 25 to 80% by weight of aluminum oxide ($Al_2O_3$),
from 20 to 75% by weight of oxygen-comprising compounds of copper, calculated as CuO,
from 0 to 2% by weight of oxygen-comprising compounds of sodium, calculated as $Na_2O$, and
less than 5% by weight of oxygen-comprising compounds of nickel, calculated as NiO.

18. The process according to claim 1, wherein the catalytically active composition of the catalyst before reduction with hydrogen comprises less than 1% by weight of oxygen-comprising compounds of nickel, calculated as NiO.

19. The process according to claim 1 any of the preceding claims, wherein the catalytically active composition of the catalyst before reduction with hydrogen comprises less than 1% by weight of oxygen-comprising compounds of cobalt, calculated as CoO.

20. The process according to claim 1, wherein the catalytically active composition of the catalyst before reduction with hydrogen comprises
from 30 to 70% by weight of aluminum oxide ($Al_2O_3$) and
from 30 to 70% by weight of oxygen-comprising compounds of copper, calculated as CuO.

21. The process according to claim 1, wherein the catalytically active composition of the catalyst before reduction with hydrogen comprises from 0.05 to 1% by weight of oxygen-comprising compounds of sodium, calculated as $Na_2O$.

22. The process according to claim 1, wherein the catalytically active composition of the catalyst does not comprise any nickel, cobalt and/or ruthenium.

23. The process according to claim 1, wherein the reaction is carried out isothermally with a temperature deviation of not more than +/−8° C.

24. The process according to claim 1, wherein hydrogen ($H_2$) is fed into the reactor in reaction step (i).

25. The process according to claim 9, wherein the reaction in reaction step (i) is carried out in a tube reactor.

26. The process according to claim 9, wherein the reaction in reaction step (i) is carried out in a shell-and-tube reactor or in a single line plant.

27. The process according to claim 1, wherein the reaction in reaction step (i) is carried out at an absolute pressure in the range from 50 to 150 bar.

28. The process according claim 1, wherein, in reaction step (i), methanol is used in a from 1- to 25-fold molar amount based on the amino alcohol (II, IIa) used.

29. The process according to claim 1, wherein the catalyst is arranged as a fixed bed in the reactor.

\* \* \* \* \*